(12) United States Patent
Curley et al.

(10) Patent No.: US 7,456,942 B1
(45) Date of Patent: Nov. 25, 2008

(54) DYNAMIC REFRACTOMETER

(76) Inventors: Michael J. Curley, 4110 Triana Blvd. #198, Huntsville, AL (US) 35805; Sergey S. Sarkisov, 2305 Fleer Cir., Huntsville, AL (US) 35803

(*) Notice: Subject to any disclaimer, the term of this patent is extended or adjusted under 35 U.S.C. 154(b) by 187 days.

(21) Appl. No.: 11/582,625

(22) Filed: Oct. 17, 2006

(51) Int. Cl.
*G01N 21/41* (2006.01)

(52) U.S. Cl. ...................................... 356/136; 356/128
(58) Field of Classification Search .......... 356/128–137
See application file for complete search history.

(56) References Cited

U.S. PATENT DOCUMENTS

| | | | |
|---|---|---|---|
| 2,807,976 A | 10/1957 | Vossberg | |
| 4,451,147 A | 5/1984 | Dobes et al. | |
| 4,844,608 A | 7/1989 | Smith | |
| 5,565,978 A | 10/1996 | Okubo et al. | |
| 5,617,201 A | 4/1997 | Kahre | |
| 5,757,477 A | 5/1998 | Nikitin et al. | |
| 5,926,284 A | 7/1999 | Naya | |
| 6,097,479 A | 8/2000 | Melendez et al. | |
| 7,283,220 B2 * | 10/2007 | Huang et al. | 356/128 |
| 2004/0145731 A1 * | 7/2004 | Nakajima et al. | 356/135 |
| 2006/0188664 A1 * | 8/2006 | Ando et al. | 428/1.1 |

OTHER PUBLICATIONS

Measurement of Thin Film Parameters with a Prism Coupler, Dec. 1973, vol. 12. No. 12, Applied Optics, pp. 2901-2908, R. Ulrich and R. Torge.

Theory of Measurement, Metricon Model 2010 Prism Coupler Thin Film Thickness/Refractive Index Measurement System Operating and Maintenance Guide Rev. (9/91); 1991 Metricon Corp. pp. 7-9.

* cited by examiner

*Primary Examiner*—Hoa Q Pham
(74) *Attorney, Agent, or Firm*—Waddey & Patterson; I.C. Waddey, Jr.

(57) ABSTRACT

A refractometer computer controls the rotation of a rotary plate upon which are mounted a prism optically coupled via an optical window to a spectroscopic cell holding a resin exhibiting a dynamic refractive index during photocuring. The computer system positions the prism and spectroscopic cell relative to a visible light laser which illuminates the prism-resin interface at selected incidence angles. A photodetector mounted on the plate generates a signal to the computer proportional to intensity of an internally reflected light beam. A curing light is selectively transmitted through the prism and into the photocurable resin. The refractometer determines the intensity of the internally reflected beam a selected incidence angles and determines the effective refractive index curve of the resin at an uncured state and, optionally, at a completely cured state. Next, an amount of uncured resin and selected optical components to be joined by the resin is placed in the spectroscopic cell and irradiated with the UV light. The refractometer is fixed at a selected incidence angle and measures the intensity of an internally reflected light beam of light throughout the cure cycle. The refractometer determines the resin's refractive index of the polymeric mixture by means of extrapolation of a horizontal shift in the effective refractive index curve of the resin from an uncured state to a selected point in the cure cycle.

31 Claims, 4 Drawing Sheets

DYNAMIC REFRACTOMETER

STATEMENT REGARDING FEDERALLY SPONSORED RESEARCH OR DEVELOPMENT

This invention was made with Government support under grant NAG8-1880 awarded by NASA. The Government has certain rights in the invention.

BACKGROUND OF THE INVENTION

The present invention relates generally to refractometers for measuring the refractive index of a translucent material during a physical or chemical process. More particularly, the invention relates to refractometers for measuring the refractive index of a transparent polymeric material during a curing process. Even more particularly, the invention relates to refractometers for continuously measuring the dynamic refractive index of a photocurable resin or adhesive mixture during the process of curing the mixture by means photonic irradiation.

Growing demand for photocurable polymeric materials has necessitated the development of advanced process monitoring techniques to ensure high quality production of cured polymers at minimum cost. In particular, monitoring the progress of the cure cycle of a photocured polymeric article during the polymerization process is critical to ensuring complete polymerization of the polymer matrix of the processed article while also providing for the shortest unit production times and the greatest production throughput of such photocured articles.

The degree of polymerization of the polymer matrix of a processed article is directly affected by various physical processing parameters. Conventionally, these parameters are varied by preset amounts over the entire curing cycle based on a predetermined cure cycle. However, even if an optimal cure cycle is determined for a given chemical composition and application, uncontrolled or unobserved variations in the temperature, pressure, and/or intensity and duration of photonic irradiation used during cure still result in variations in the degree of polymerization of the polymer matrix. It is therefore essential to reduce the effect of processing variations by active control of the cure cycle rather than simply using predetermined values for application of the processing parameters. Such a scheme requires dynamic properties of the curing polymeric mixture to be measured throughout the cure process. These measured dynamic properties would then serve as an input to a process model, which in turn would be used in situ to control the processing parameters during processing. Such a processing scheme would produce polymeric articles of consistent quality at maximum speed while reducing waste due to improper curing.

In particular, a device to continuously and accurately measure the cure process of photocurable polymers would provide an input to the process model so as to allow optimal control of selected processing parameters such as total cure time and photonic irradiation duration and intensity. One measurable dynamic parameter that accurately indicates the status of the curing process in transparent or translucent photocurable polymers is the refractive index of the polymeric material. Generally, the refractive index of a photocurable polymeric material changes predictably and continuously from the refractive index of the material in an uncured state to the refractive index of the material in a completely cured state.

Thus, there is a need for simple and fast method and device to continuously and accurately measure the changes of refractive index of a photocurable polymeric mixture during transformation from uncured raw materials into a cured polymer. Such a device and method would be of great value since photocurable polymers, such as photocurable resins and adhesives, are frequently used in a wide variety of optical applications such as assembling optical components, making compound lenses, creating and connecting optical fibers, fixing fibers in mechanical splices, and other similar applications.

Refractometers are one class of devices commonly used to measure refractive index of materials. In general, refractometers measure the critical angle of total reflection by directing an obliquely incident beam of light at a surface-to-surface boundary between a high refractive index prism and a translucent sample to allow a portion of the light to be observed after interaction at the boundary. Reflected light refractometers detect and measure the light that is reflected at the surface-to-surface boundary. In prior art reflected light refractometers, an illuminated region is produced over a portion of a detection field of view, and the location of a shadowline between the illuminated region and an adjacent dark region in the detection field of view allows the sample refractive index to be deduced geometrically.

Current devices used to measure the changes of refractive index during the cure cycle of photocurable polymers include classical ABBE Type refractometers. ABBE Type refractometers measure either the refractive index of the liquid polymeric resin prior to initiation of the cure process or measure the refractive index of the cured polymer after the completion of the curing process. A significant time delay between the change of the refractive index and the moment when the data is obtained makes real time or even near-real time measurement of the kinetics of the refractive index change during the photo-curing process impossible.

Prior art refractometers include a prism coupler described in paper R. Ulrich and R. Forge. "Measurement of thin film parameters with a prism couple", Appl. Optics 12 (1973) 2901-2908 and a prism coupler found in the Metricon 2010 made by Metricon Corporation, P.O. Box 63 Pennington, N.J. 08534, telephone 609-737-1052. The principle of operation used in these two prior art devices is based on the measurement of the critical angle of total internal reflection. A material with unknown refractive index is put in contact with the long side face of a rectangular isosceles prism. The prism must have refractive index greater than of the material. A laser beam enters the prism from one of its short side faces. The beam strikes the interface between the resin and the prism and is reflected due to the total internal reflection towards the second short side face of the prism. After exiting the prism the beam strikes a silicon photodetector, which generates signal proportional to the intensity of the beam. The prism, together with the resin in contact with it, are mounted on a rotary table which rotates with respect to the fixed laser beam until the intensity of the totally internally reflected portion of the beam sharply drops down. The angle of incidence of the beam striking the interface at this position of the prism is equal to the critical angle of reflection. The unknown refractive index of the material could be calculated using the known index of the coupling prism and the critical angle.

One disadvantage of these prior art measurement instruments is that the measurement of the refractive index using these devices is inherently static. Measurement of any change of the refractive index must be based on the change in the critical angle. Changes in the critical angle require a separate series of rotations of the prism for each discrete measurement and also require, for each discrete measurement, determination of the change in the angular displacement at which the intensity of totally internally reflected beam abruptly changes as compared to the previous discrete measurement. Such, rotation, either manual or automatic, is a time consuming procedure that is not suitable for continuous tracking of the changing critical angle. A second disadvantage is that the prior art devices do not incorporate a source of photonic radiation with the mechanism for measuring refractive index of the photocurable polymeric materials. Combining both functions into one device would provide a highly desirable economy in the cost of equipment.

What is needed, then, is a refractometer which provides continuous, real-time measurements of the dynamic changes in the refractive index of a translucent photocurable material during the curing process.

Additionally, what is needed is a refractometer which provides continuous, real-time measurements of the dynamic changes in the refractive index of a translucent photocurable material during the curing process and which provides a source of photonic irradiation for curing the material.

Yet additionally, what is needed, is a system or method for controlling the processing parameters during the process of curing a translucent photocurable material wherein the system or method incorporates a refractometer to provide continuous, real-time measurements of the dynamic changes in the refractive index of the translucent photocurable material and further provides an apparatus or steps to adjust the processing parameters of the curing process based on such measurement of real-time changes in refractive index.

BRIEF SUMMARY OF THE INVENTION

The refractometer of the present invention includes a prismatic optical element optically coupled to a spectroscopic cell for holding a photocurable polymeric mixture during the process of curing the polymeric mixture. The polymeric mixture exhibits a dynamic refractive index that changes generally continuously during the curing process from an initial value to final value. The spectroscopic cell is optically coupled to a prismatic optical element so as to provide for the illumination of the interface between the prismatic optical element and the resin within the spectroscopic cell and the generation of internally reflected light at such interface. In preferred embodiments of the invention, the refractometer includes a source of measurement light illuminating the prismatic optical element with a measurement light beam and a light detecting and measuring element for detecting and measuring the intensity of the internally reflected portion of the measurement light beam.

The refractometer of the present invention further includes a curing means adapted to a cure polymeric mixture held in the spectroscopic cell. In preferred embodiments the polymeric mixture is a photocurable polymeric mixture and the curing means correspondingly includes a source of photonic radiation and a light transmission conduit adapted to channel the photonic radiation through the prismatic optical element and into the polymeric mixture within the spectroscopic cell. Thus, the prismatic optical element is used as an optical conduit for both the measuring light beam and the curing photonic radiation.

In one preferred embodiment the photocurable polymeric mixture is a photocurable polymer resin or adhesive. The spectroscopic cell includes container having an optical window that is optically coupled to a prism of cubic zirconium. The source of measurement light illuminating the prism is a laser that emits a tuned measurement laser beam. The measurement laser beam enters the prism and is refracted to an interface between the resin and the prism at an incidence angle θ. The measurement laser beam undergoes either partial or total internal reflection as a function of the incidence angles θ and the effective refractive index of the resin. The internally reflected beam is reflected from the through and exits the prism. In one preferred embodiment, the source of photonic radiation and a light transmission conduit includes an optical fiber that transmits the UV light of a UV lamp to a collimator. The collimated beam of UV light is transmitted through the prism and into the photocurable polymeric resin held in the spectroscopic cell. This UV radiation causes photocuring of the resin and causes the refractive index of the resin to change throughout the curing process.

The intensity I of the internally reflected beam is a function of the incidence angle θ such that the intensity I increases as the incidence angel θ increases and approaches the critical incidence angle $θ_c$ and the intensity I reaches a plateau when θ equals or exceeds $θ_c$. In one preferred embodiment, the light detecting and measuring element is a silicon photodetector that is connected through an interface to a computer system adapted to continuously determine the measured intensity I of the internally reflected beam and the dynamic change thereof during the curing cycle without rotation of the prism relative to the measurement light beam.

The refractometer of the present invention is adapted to determine the intensity I of the internally reflected beam a selected incidence angles θ and to determine the effective refractive index $n_{eff}$ curve of photocurable polymeric mixture at an uncured state and, optionally, at a completely cured state. According to the method of the present invention, a test sample amount of a selected composition of a photocurable polymeric mixture is disposed within the spectroscopic cell. The prismatic optical element coupled to the spectroscopic cell are rotated relative to the source of measurement light at selected incidence angles θ and the intensity I of the internally reflected light beam at selected incidence angles θ is measured and recorded. Next, the refractive index of the uncured resin $n_r^{(i)}$ is experimentally determined.

According to the further method of present invention, a completely cured test sample amount of the polymeric mixture is disposed within the spectroscopic cell and the steps of measuring and recording the intensity I of the internally reflected light beam at selected incidence angles θ is repeated. The cured test sample amount of the selected resin is disposed in the spectroscopic cell which is rotated through selected and recorded incidence angles θ as described above. Next, the refractive index of the cured resin $n_r^{(f)}$ is experimentally determined.

The refractometer is further adapted to continuously measure the change in intensity of an internally reflected measurement beam of light fixed at a selected incidence angle θ throughout the cure cycle and, at selected points in the cure cycle, to determine: the resultant change of the critical incidence angle $θ_c^{(t)}$; the resultant the change of the refractive index of the polymeric mixture $Δn_r^{(t)}$; and the resultant refractive index of the polymeric mixture $n_r^{(t)}$ by means of a novel procedure of extrapolation of the data points the of the refractive index of the polymeric mixture $n_r$ described herein.

DETAILED DESCRIPTION OF THE INVENTION

Figure 1:
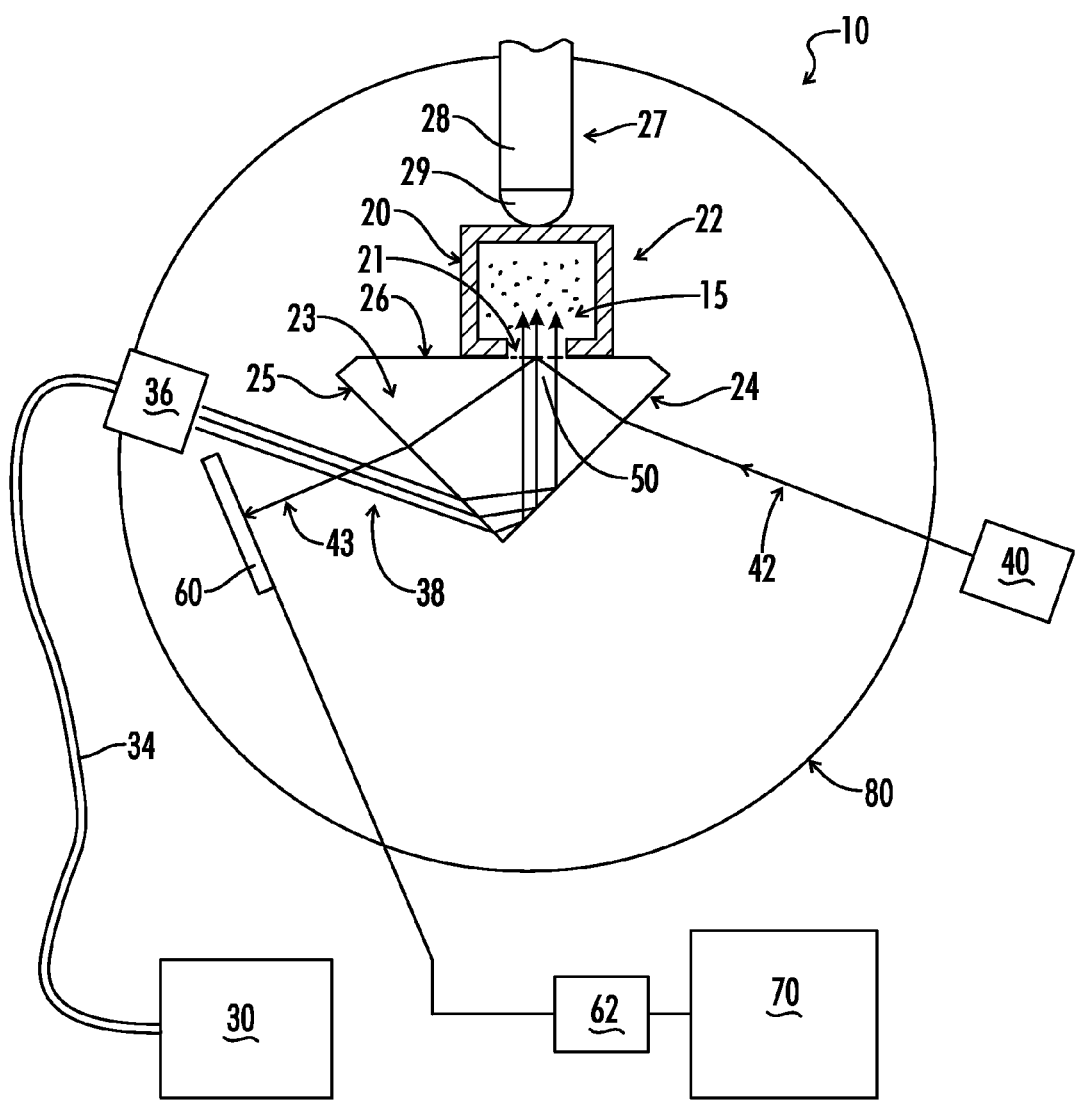
FIG. 1 shows a preferred embodiment of the present invention.

As shown in FIG. 1, the present invention is a novel refractometer 10 and includes a spectroscopic cell 22 for holding a polymeric mixture during the process of curing the polymeric mixture. The polymeric mixture exhibits a dynamic refractive index that changes generally continuously during the curing process from an initial refractive index of an uncured polymeric mixture to a final refractive index of a completely cured polymeric mixture. In one preferred embodiment the polymeric mixture is a photocurable polymer resin. In an alternate preferred embodiment the polymeric mixture is a photocurable adhesive. In the preferred embodiment shown in FIG. 1, a photocurable polymer resin 15 is held in a spectroscopic cell 22 used to splice optical fibers. The spectroscopic cell 22 includes rectangular container 20 having an optical window 21 disposed within one wall of the container 20. Optionally the spectroscopic cell 22 holds selected optical elements to be bonded or spliced by the resin or adhesive during the curing process.

In the present invention the spectroscopic cell is disposed so as to be optically coupled to a prismatic optical element having a refractive index that is greater than the refractive index of the polymeric mixture. In one preferred embodiment shown in FIG. 1, the optical window 21 of the spectroscopic cell 22 is disposed against a coupling prism 23. The container 20 of the spectroscopic cell 22 is pressed against the coupling prism 23 by a holding device 27. In one preferred embodiment, the holding device 27 includes a piston 28 having a rounded pressure knob 29 at one end. The piston 28 contains a compressed gas, such as air, that provides a motive force for biasing the pressure knob 29 against the container 20 so as to hold the optical window 21 of the spectroscopic cell 22 against the prism 23. In alternate embodiments of the present invention, the holding device is a clamping assembly. Other holding devices may be readily selected and employed in the present invention by one skilled in the arts. In other alternate embodiments of the present invention, the holding device is omitted and the prismatic optical element is integral to the spectroscopic cell. In preferred embodiments of the invention, the prismatic optical element includes a prism with multiple sides.

In one preferred embodiment shown in FIG. 1, the spectroscopic cell 22 is held against the coupling prism 23 and the optical window 21 of the cell is a cavity disposed within one wall of the container 20 so as to allow the resin 15 to form an optical interface with the coupling prism 23. In another preferred embodiment, the optical window 21 is a transparent plate and the photocurable polymer resin 15 is disposed adjacent to an interior surface of the transparent plate so as to form an optical interface with the optical window. The transparent plate is preferably formed of glass. Alternately, the transparent plate may be formed of other suitable optical materials readily known to one skilled in the arts.

The prism 23 has a first short side face 24, a second short side face 25 and a long side face 26. The long side face 26 is preferably coupled with the optical window 21 of the spectroscopic cell 22. In one preferred embodiment, the prism 23 is made of cubic zirconia. However, one skilled in arts will recognize that the present invention is not limited to cubic zirconia prisms but encompasses any suitable prismatic optical element composed of any suitable prismatic materials as are readily known in the arts.

The spectroscopic cell is optically coupled to the prismatic optical element so as to provide for the illumination of the interface between the prismatic optical element and the resin within the spectroscopic cell and the generation of internally reflected light at such interface. Measurement of selected characteristics of the internally reflected light provides information for the determination of the index of refraction of the resin. In one preferred embodiment of the present invention, the refractometer includes a source of measurement light illuminating the prismatic optical element with a measurement light beam. In the preferred embodiment shown in FIG. 1, the source of measurement light is a laser 40 that emits a laser beam 42. In a prototype of the embodiment shown in FIG. 1, the laser is a red He—Ne laser that emits a tuned red laser beam. Alternate embodiments of the present invention include a plurality of sources of measurement light wherein each source illuminates the prismatic optical element with a measurement light beam. In other alternate embodiments of the present invention, the refractometer includes a source of measurement light adapted to operate at various selected wavelengths. One preferred alternate embodiment includes a plurality of lasers illuminating a prism optically coupled to a spectroscopic cell at selected incidence angles θ, each laser emitting a measurement laser beam of a different selected wavelength. Another preferred alternate embodiment includes a tunable light source selectably operating at various selected wavelengths of measurement light.

Figure 2:
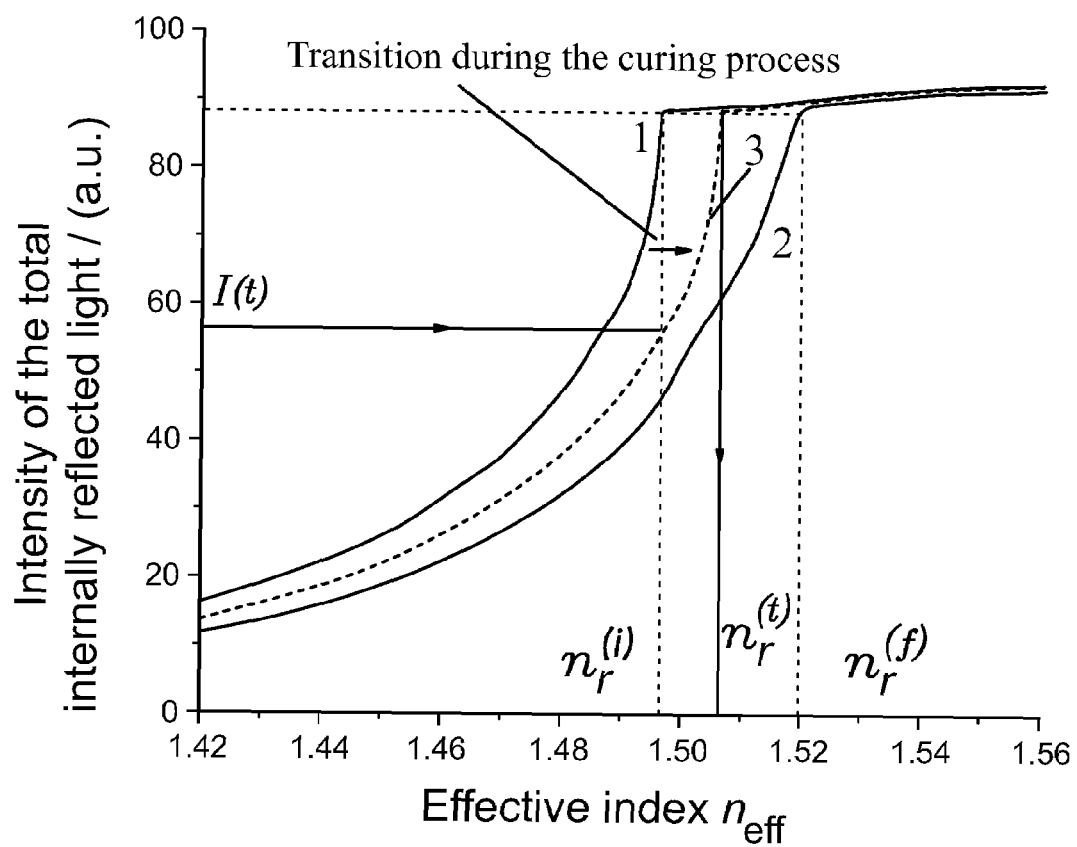
FIG. 2 is a graph of experimental data showing the refractive index of a photocurable resin at selected points in the cure cycle as a function of the intensity of the totally internally reflected light.

Referring again to the refractometer 10 shown in FIG. 1, the laser beam 42 emitted by the measurement laser 40 enters the prism 23 through the first short side face 24 of the prism and is refracted to the interface 50 between the resin 15 and the long side face 26 of the prism 23. According to the well understood principles of refraction of light in a transparent media, the red laser beam 42 arrives at the interface 50 at an incidence angle θ as measured away from the normal direction from the plane tangent to the interface 50. At this interface 50 the red laser beam 42 undergoes either partial or total internal reflection. At incidence angles θ below an experimentally determined critical incidence angle $\theta_c$: $\theta > \theta_c$, the red laser beam 42 undergoes only partial internal reflection and a portion of laser beam 42 is transmitted into the resin 15 through the optical window 21 in the spectroscopic cell 22. Another portion of the laser beam 42 remains within the prism 23 as an internally reflected beam 43. This internally reflected beam 43 is reflected from the long side face 26 at an angle corresponding to the incidence angle θ through the prism 23 and exits the prism through the second short side face 25 where it is refracted a second time. It is well understood that at incidence angles θ above the critical incidence angle $\theta_c$: $\theta > \theta_c$, the red laser beam 42 undergoes substantially total internal reflection. Thus, the intensity I of the internally reflected beam 43 is a function of the incidence angle θ. As is shown in FIG. 2, the intensity I of the internally reflected beam 43 increases as the incidence angle θ increases and approaches the critical incidence angle $\theta_c$ and the intensity I of the internally reflected beam 43 reaches a plateau when θ equals or exceeds $\theta_c$.

The refractometer further includes a light detecting and measuring element for detecting and measuring the intensity of the internally reflected portion of the measurement light beam. Referring again to FIG. 1, the internally reflected beam 43 exits the second short side face 25 and strikes a silicon photodetector 60 which in turn generates an electrical signal proportional to the intensity I of the reflected beam 43. In the preferred embodiment shown in FIG. 1, the photodetector 60 is connected through interface 62 to a computer system 70. The computer system 70 is adapted to continuously determine the measured intensity I of the internally reflected beam 43 and the dynamic change thereof. The computer system 70 is further adapted to continuously determine the critical incidence angle $\theta_c$, the refractive index of the resin $n_r$, the change of the critical incidence angle $\theta_c$ and the change of the refractive index of the resin $n_r$ by means of a novel procedure of extrapolation of the data points the of the refractive index of the resin $n_r$ described infra.

The refractometer of the present invention further includes a curing means adapted to cure the polymeric mixture held in the spectroscopic cell. According to the present invention, the curing means is may be any conventional means or combination of conventional means that control any of the various physical processing parameters used during the curing process of the polymeric materials, including: time; intensity and duration of photonic and/or ultrasonic irradiation; temperature, and pressure; and combinations thereof. In preferred embodiments of the present invention, the polymeric mixture is a photocurable polymer resin and the curing means correspondingly includes a source of photonic radiation. In more preferred embodiments of the present invention, the polymeric mixture is a photocurable polymer and the source of photonic radiation is a source of UV radiation. In the preferred embodiment shown in FIG. 1, the source of UV radiation UV lamp 30 which emits UV light that is variable in its intensity and duration.

The curing means of the present invention also includes a light transmission conduit adapted to channel the photonic radiation into the spectroscopic cell. In one preferred embodiment, the light transmission conduit includes a fiber optic means that receives and transmits the photonic radiation from the source of photonic radiation. In the preferred embodiment shown in FIG. 1, fiber optic means includes a fiber optic cable 34 that receives UV light from the UV lamp 30 and transmits the light to a collimator 36 which emits a collimated beam of UV light 38.

In one preferred embodiment of the invention, the light transmission conduit includes an optical window disposed in the spectroscopic cell so as to allow transmission of the photonic radiation into the photocurable polymer held in the spectroscopic cell. In a more preferred embodiment of the invention, the light transmission conduit further includes a prismatic optical element optically coupled to an optical window disposed in the spectroscopic cell so as to allow transmission of the photonic radiation into the photocurable polymer held in the spectroscopic cell. In yet more preferred embodiments of the invention, the light transmission conduit incorporates the same prismatic optical element as is used to refract and internally reflect the measurement light beam of the invention. As shown in FIG. 1, the light transmission conduit includes the prism 23 of one preferred embodiment. The collimator 38 of the reflectometer 10 shown in FIG. 1 emits a collimated beam of UV light 38 that is transmitted through the second short side face 25 and then refracted through prism 23. Optionally, the collimated beam of UV light 38 may be transmitted through the first short side face 24 and then refracted through prism 23. Referring again to FIG. 1, the beam 38 is totally internally reflected at the first short side face 24 and transmitted into the long side face 26. The beam of UV light 38 escapes the prism through the long side face 26 and is transmitted through the optical window 21 into the photocurable polymeric resin 15 held in the spectroscopic cell 22. This irradiation causes photocuring of the resin 15 and causes the refractive index of the resin 15 to change throughout the curing process.

In accordance with the present invention, the curing means may be optionally adapted to emit light of selectable intensity, pulse length, frequency or combinations thereof for selected periods of radiation and selectable total duration of radiation. In one preferred optional embodiment, the UV light source emits a UV light having an intensity that is selectably controlled by a control means. Similarly, in another preferred optional embodiment, the UV light source is controlled by a control means so as to selectably vary the frequency and duration of periods of radiation, the total cumulative duration of radiation or combinations thereof during which the UV light source emits UV light into the photocurable polymeric mixture held in the spectroscopic cell. Alternate embodiments include a plurality of sources of UV radiation adapted for transmission into a photocurable polymeric mixture held in the spectroscopic cell by means of one or more light transmission conduits. Other alternate embodiments of the present invention include a plurality of selectable sources of UV radiation, each sources adapted to cure a different composition of a photocurable polymeric mixture.

During the process of photocuring of the resin or other photocurable polymeric mixture, the refractive index of the resin increases from its initial value $n_r^{(i)}$ to the final value of $n_r^{(f)}$. Correspondingly, the critical incidence angle $\theta_c$ increases as a function of the increase in the refractive index of the resin. The critical incidence angle $\theta_c$ must satisfy to the equation: $\sin \theta_c = n_r/n_p$, where $n_r$ is the refractive index of the resin and $n_p$ is the refractive index of the prism.

An effective refractive index $n_{eff}$ can be determined as a function of the refractive index of the prism $n_p$ and of the incidence angle $\theta$ by the equation: $n_{eff} = n_p \sin \theta$. For a polymeric mixture at a selected point of cure t in the curing cycle and for a known refractive index of the prism $n_p$, experimental measurement of the intensity I of the internally reflected light beam 42 at selected incidence angles $\theta$ determines the effective refractive index at each incidence angle $\theta$, as shown in Curves 1 and 2 of the effective refractive index $n_{eff}$ as shown in FIG. 2. For each of Curves 1 and 2, the effective refractive index $n_{eff}$ becomes equal to the refractive index of the polymeric mixture $n_r$ when $\theta = \theta_c$. Thus, the refractive index of the uncured polymeric mixture $n_r^{(i)}$ can be experimentally determined as the effective refractive index $n_{eff}$ at the point of discontinuity between the continuously rising of the region of Curve 1 where the selected incidence angles $\theta$ are less than the critical incidence angle $\theta c$ and the plateau region of Curve 1 where the selected incidence angles $\theta$ are equal to or greater than the critical incidence angle $\theta c$. This relationship holds at any point in the curing cycle, including the final point where the polymeric mixture is completely cured, where the refractive index of the cured polymeric mixture $n_r^{(f)}$ can be experimentally determined as the effective refractive index $n_{eff}$ at the point of discontinuity between the continuously rising of the region of Curve 2.

Both Curve 1 and Curve 2 may be experimentally determined by rotating the prismatic optical element coupled to the spectroscopic cell relative to the source of measurement light as a means of determining the selected incidence angles $\theta$ and the intensity I of the internally reflected light beam 42 at selected incidence angles $\theta$. The refractometer is optionally configured to provide rotation of the assembly of the prismatic optical element coupled to the spectroscopic cell relative to the source of measurement light. In the preferred embodiment shown in FIG. 1, the spectroscopic cell 22, prism 23, the holding device 27, the collimator 36 and detector 60 of the refractometer 10 are mounted on a rotary table 80 which is optionally controlled in angular displacement by computer system 70.

According to one step in the method of the present invention, a test sample amount of a selected composition of a photocurable polymeric mixture is disposed within the spectroscopic cell. The prismatic optical element coupled to the spectroscopic cell are rotated relative to the source of measurement light at selected incidence angles θ and the intensity I of the internally reflected light beam 42 at selected incidence angles θ is measured and recorded. In one step of one preferred method of the present invention, a test sample amount of a selected photocurable resin 15 is disposed in the spectroscopic cell 22. The prism 23 and the spectroscopic cell 22 are rotated through selected and recorded incidence angles θ relative to the measurement laser beam 42. According to a preferred method, computer system 70 controls the rotary table 80 to rotate the prism 23 and the spectroscopic cell 22. According to the present invention, the intensity I of the internally reflected light beam 42 at the selected and recorded incidence angles θ is measured and recorded. Next, the refractive index of the uncured resin $n_r^{(i)}$ is experimentally determined as the effective refractive index $n_{eff}$ at the point of discontinuity in Curve 1 of FIG. 2 as described above. Notably, in these steps the curing means is not operated.

The test sample amount of the photocurable polymeric mixture is next completely cured and is disposed within the spectroscopic cell. In the preferred method, UV lamp 30 is operated at a sufficient intensity and duration to completely cure the test sample amount of the photocurable polymeric mixture.

According to another step in the method of present invention, the completely cured test sample amount of the polymeric mixture is disposed within the spectroscopic cell and the steps of measuring and recording the intensity I of the internally reflected light beam 42 at selected incidence angles θ is repeated. In the preferred method of the present invention, the cured test sample amount of the selected resin 15 is disposed in the spectroscopic cell 22 which is rotated through selected and recorded incidence angles θ as described above. Next, the refractive index of the cured resin $n_r^{(f)}$ is experimentally determined as the effective refractive index $n_{eff}$ at the point of discontinuity in Curve 2 of FIG. 2 as also described above.

Referring to FIG. 2, Curve 1 and Curve 2 form the boundary conditions for determination of the refractive index of the photocurable polymeric mixture during the curing process. During the process of curing the resin 15, the refractive index of the resin increases from its initial value $n_r^{(i)}$ to the final value of $n_r^{(f)}$. At a given point of cure in the cure cycle the corresponding the effective refractive index $n_{eff}$ curve (Curve 3 of FIG. 2) displays a shift along the $n_{eff}$ axis from Curve 1 that is generally equivalent to the change in the refractive index of the resin at the given point in the cure cycle $n_r^{(t)}$ from the refractive index of the resin at the initial point in the cure cycle $n_r^{(i)}$.

One of the advantages of the present invention is that the intensity I of the internally reflected light beam can be quickly and repeatedly measured during the photocuring process and the refractive index $n_r$ of the of photocurable polymeric mixture can be continuously determined during the photocuring process without the excessive delays associated mechanical rotation of the prisms taught by the prior art devices and methods. Thus, according to the method of the present invention, a working amount of a selected composition of a photocurable polymeric mixture is disposed within the spectroscopic cell along with any desired additional optical elements to be integrated with the cured polymeric mixture. The prismatic optical element coupled to the spectroscopic cell are rotated relative to the source of measurement light to selected incidence angle θ, preferably the incidence angle θ previously determined to correspond to refractive index of the uncured resin $n_r^{(i)}$, and the intensity I of the internally reflected light beam is measured and recorded during the cure process. In the preferred method of the present invention, the working amount of a selected photocurable resin 15 is disposed in the spectroscopic cell 22 along with any desired additional optical elements to be integrated with the cured resin. (For example, two ends of fiber optic cables may be placed within the spectroscopic cell 22 to be held together in a splice by the resin when cured.) The prism 23 and the spectroscopic cell 22 are rotated to the incidence angle θ previously determined to correspond to refractive index of the uncured resin $n_r^{(i)}$: $n_{eff}=n_r^{(i)}$. UV lamp 30 is operated at selected intensities and periods and the photocurable resin 15 undergoes a curing cycle. During the curing cycle the optically coupled prism 23 and spectroscopic cell 22 are held stationary with regards to the laser beam 42 and the laser 40.

Figure 3:
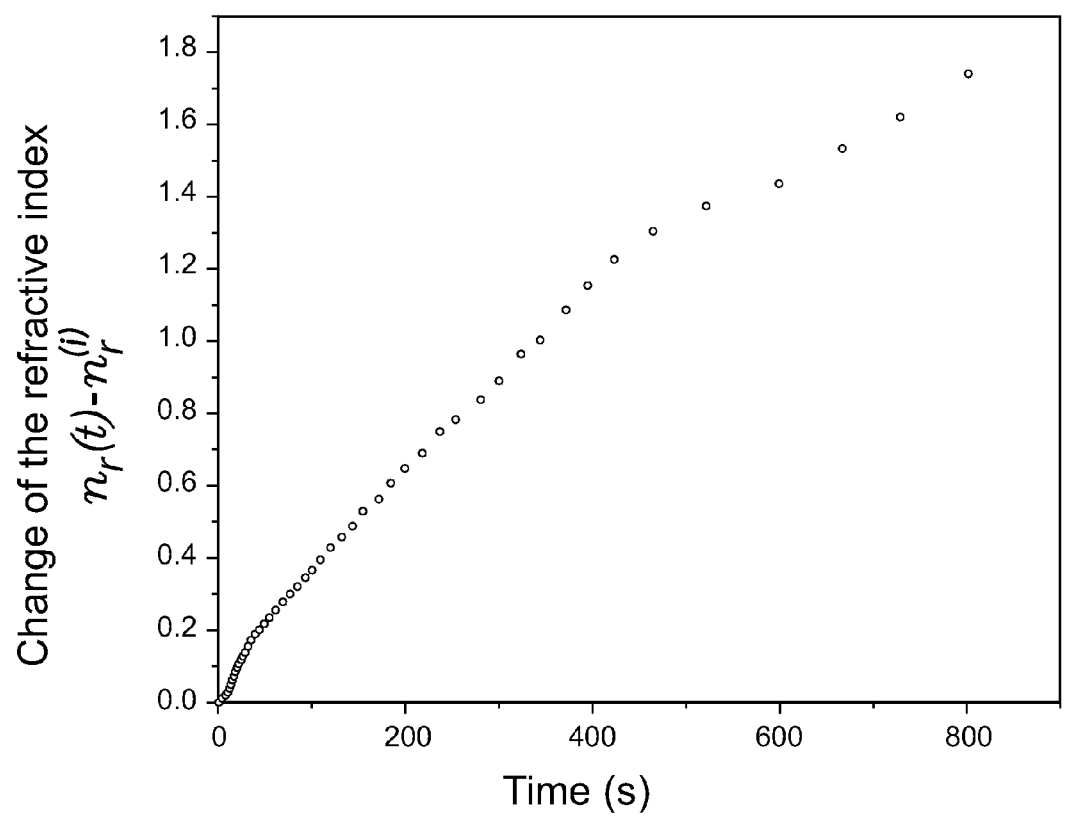
FIG. 3 is a graph experimental data showing the change of the refractive index of a photocurable resin as a function of time during the curing cycle.

According to a step in the method of the present invention, the internally reflected measurement beam of light is fixed at critical incidence angle $\theta_{c(i)}$ of the uncured polymeric mixture and throughout the cure cycle. A sampled point of cure t in the cure cycle may be understood to be any convenient parameter including: elapsed time of cure, total duration of irradiation, total energy of irradiation, or change in the intensity I of the internally reflected light beam during the photocuring process. According to a preferred step in the method of the present invention, the intensity $I_{(t)}$ of the internally reflected light beam is measured during the curing cycle and recorded as a function of time. (Here the sampled point of cure t in the cure cycle corresponds to the time parameter) Assuming that the intensity I of internally reflected light as a function of the effective index $n_{eff}$ corresponding to selected incidence angles θ as describing the increasing part of each of the Curves 1, 2 and 3 before the plateau is reached does not change except for the horizontal shift at the transition from Curve 1 toward Curve 2 as the I function is horizontally displaced until it intersects with vertical line $n_r=n_r^{(t)}$ at the point $I=I_{(t)}$ as shown in FIG. 2. Thus, the refractive index of the resin $n_r^{(t)}=n_{eff}$ where the Curve 3 reaches plateau. FIG. 3 shows a graphical determination of the refractive index of the resin $n_r^{(t)}$ as a function of time during the curing cycle where the UV irradiation is of a constant intensity. Thus, at each sampled point of cure t in the cure cycle, the intensity $I_{(t)}$ is compared to the intensity $I_{(i)}$ corresponding the effective refractive index $n_{eff}$ curve (Curve 3 of FIG. 2). Curve 3, as stated supra, displays a shift along the $n_{eff}$ axis from Curve 1 that is generally equivalent to $\Delta n_r^{(t)}$ the change in the refractive index of the resin at the sampled point of cure t in the cure cycle from the refractive index of the resin at the initial point in the cure cycle $n_r^{(i)}$. The refractive index of the resin at the sampled point of cure t in the cure cycle is determined by the equation $n_r^{(t)}=\Delta n_r^{(t)}+n_r^{(i)}$. The preferred method of the present invention contemplates determination of the refractive index of the resin $n_r^{(t)}$ at the sampled point of cure t by conventional means of data analysis. This method may be automated by means of a computer system.

The refractometer is optionally adapted to control the source of photonic radiation and a light transmission conduit to adjust at least one of the duration, intensity, operating frequency, and period of the photonic radiation in response to the determination of the resultant refractive index $n_r^{(t)}$ of the polymeric mixture.

Figure 4:
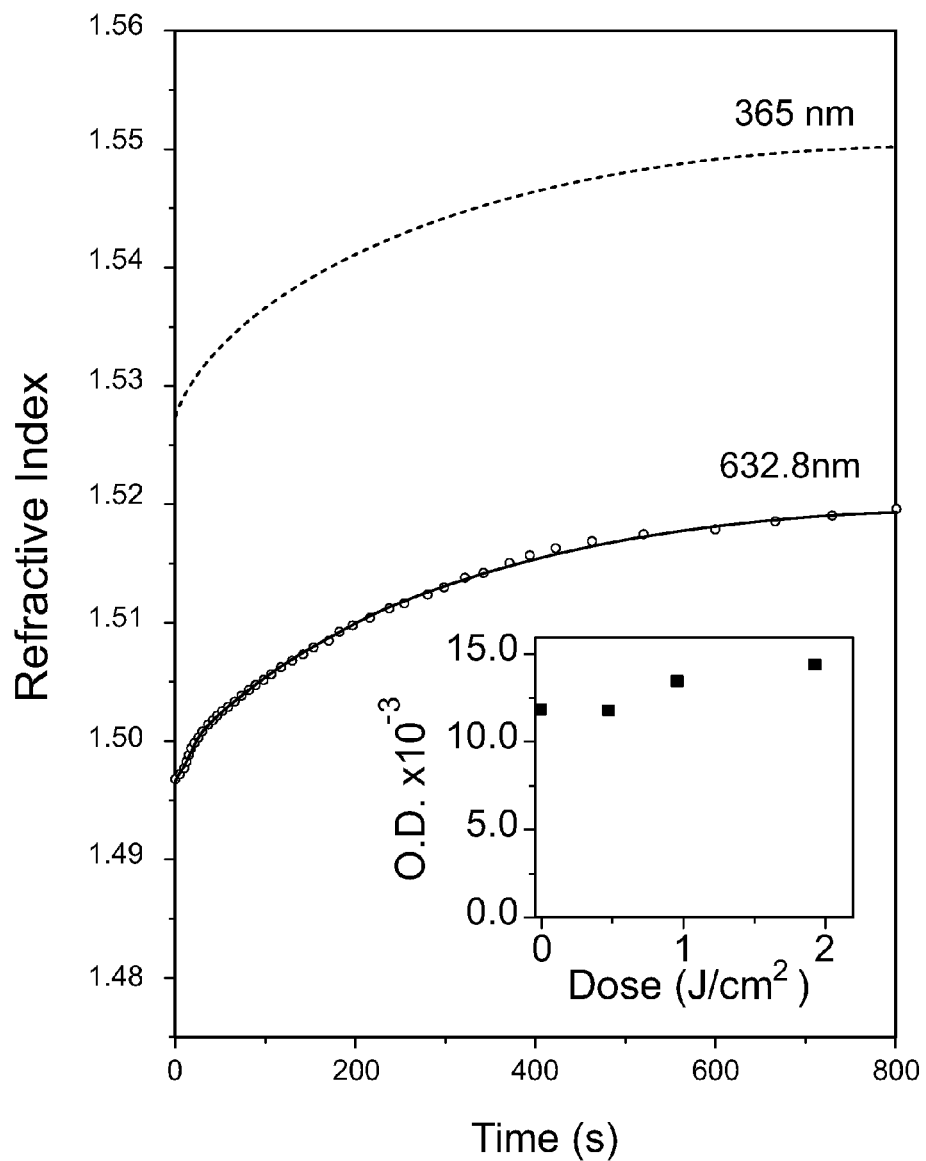
FIG. 4 is a graph of experimental data showing the refractive index of a photocurable resin at selected

The inventors have constructed a prototype of the refractometer 10 shown in FIG. 1 and have experimentally verified the operability and assumptions by measuring the kinetic changes of the refractive indices of two photocurable resins during the process of photocuring.: Resins SL 5195 and SL 8195, which were obtained from Vantico A&I US, Inc. 4917 Dawn Ave., East Lansing, Mich. FIG. 4 shows a graphic plot of the refractive index of the SL 5195 resin irradiated at 632.8 nm UV light from the UV lamp. The radiation from the UV lamp was sent through a 365 nm filter. The solid line of the graphic plot is the nonlinear fit of the experimental data. The dotted line is the approximation of the refractive index at the 365 nm as a function of time during the curing cycle where the UV radiation is of a constant intensity. The intensity of the UV radiation was $1.7\ 10^{-4}$ W/cm$^2$. The inset of the graphical data shows the optical density (O.D.) of a 17 μm thick film of the SL 5195 resin versus the dose of exposure. The prototype of the refractometer of the present invention was used to measure the change of the index of refraction within the range of 1.3 to 1.8 at a wavelength within the range from 400 nm to 1550 nm with a time constant of the measurement of the refractive index at a certain moment of time being 0.1 sec or less.

The inventors have experimentally verified the assumption that the intensity I of internally reflected light function describing the increasing part of the Curves 1, 2 and 3 in FIG. 1 does not change except for the horizontal shift at the transition from Curve 1 to Curve 2 as the intensity I of internally reflected light function is horizontally displaced until it intersects with vertical line $n_r = n_r^{(t)}$. FIG. 3 shows the resulting determination of the change of the refractive index of the SL 8195 resin versus the time of curing.

Providing a photocuring means having a photonic radiation of a constant intensity is one preferred step in the method of the present invention. The preferred embodiment includes providing a constant intensity UV lamp as the curing means. However, the present invention encompasses apparatus and methods that provide selectable variations in the intensity, period and duration of the photonic irradiation. The present invention contemplates determination of the change of the refractive index of a selected photocurable polymeric mixture at the given point in the cure cycle $n_r^{(t)}$ as a function of any suitable parameter for t. For example, the parameter t may be taken to be total duration of irradiation. Alternative, t may be taken to be a measure of total amount of photonic energy deposited within the photocurable polymeric mixture. This latter parameter may be useful where the intensity, duration and/or period of radiation are variable.

One preferred alternate embodiment of the refractometer of the present invention includes a source of radiation, such as an adjustable UV lamp that is selectable in any of the intensity of radiation, the length of period of irradiation, the total duration of radiation, or a combination thereof. This alternate embodiment of the refractometer of the present invention further includes a computer system adapted to determine the total amount of photonic energy deposited within the photocurable polymeric mixture at a selected point t in the cure cycle by the adjustable UV lamp. The computer system of this alternate embodiment is further adapted to determine the refractive index $n_r^{(t)}$ of the photocurable polymeric mixture at the selected point t in the cure cycle as a function of total amount of photonic energy deposited. The computer system of this alternate embodiment is yet further adapted to adjust any of any of the intensity of irradiation, the length of period of irradiation, the total duration of irradiation, or a combination thereof in response to the refractive index $n_r^{(t)}$ of the photocurable polymeric mixture at the selected point t in the cure cycle.

Thus, although there have been described particular embodiments of the present invention of a new and useful Dynamic Refractometer, it is not intended that such references be construed as limitations upon the scope of this invention except as set forth in the following claims.

What is claimed is:

1. A refractometer comprising:
   spectroscopic cell including a container adapted to hold a photocurable mixture;
   a prismatic means having an interface surface disposed adjacent an optical window disposed in the container;
   a measurement light source adapted to emit a measurement light beam, the measurement light beam illuminating the interface surface at selectable incidence angles so as to reflect a portion of the measurement light beam as an internally reflected light beam;
   a light detection means disposed so as to receive the internally reflected light beam; and
   a photonic curing means adapted to selectively emit a curing light beam and disposed so as to irradiate the photocurable mixture with the curing light beam.

2. The apparatus of claim 1, wherein the prismatic means comprises a prism having a plurality of sides, including a first side comprising the interface surface,
   wherein, the prism is disposed so as to receive the measurement light beam through the second side and adapted to emit the internally reflected light beam from a third side, and
   wherein, the prism is disposed so as to receive the curing light beam through at least one face and adapted to emit the curing light beam from the first face through the optical window and into the photocurable polymeric material.

3. The apparatus of claim 2, wherein the prism comprises cubic zirconium.

4. The apparatus of claim 2, wherein the measurement light source comprises a measurement laser, and
   wherein, the measurement light beam comprises a measurement laser beam.

5. The apparatus of claim 4, wherein the measurement laser comprises a visible light laser.

6. The apparatus of claim 4, wherein, the light measuring means comprises:
   a photon detector disposed so as to receive the internally reflected light beam and adapted to produce a signal proportional the intensity of the internally reflected light beam; and
   a computer system adapted to receive the signal provided from the photon detector and further adapted to determine the intensity of the internally reflected light beam.

7. The apparatus of claim 6, wherein, with the container holding a test amount of the photocurable mixture in a selected boundary state, the apparatus is adapted to rotate the spectroscopic cell, the prism, and the photon detector relative to the measurement laser, and
   wherein, the apparatus is further adapted to illuminate the interface surface at each of a plurality of selected incidence angles and to determine the intensity of the internally reflected light beam of the mixture in the selected boundary state at each incidence angle selected.

8. The apparatus of claim 7, wherein, the boundary state comprises an uncured state.

9. The apparatus of claim 7, wherein the boundary state comprises an cured state.

10. The apparatus of claim 7, the apparatus further comprising:
a rotation means having the spectroscopic cell, the prism, and the photon detector mounted thereon and adapted to rotate relative to the measurement laser.

11. The apparatus of claim 7, wherein the computer system is adapted to determine, for each selected incidence angle, the effective refractive index and to correlate, for each selected incidence angle, the effective refractive index and the intensity of the internally reflected light beam of the mixture in the selected boundary state.

12. The apparatus of claim 11, wherein the computer system is further adapted to determine the refractive index of photocurable mixture in the selected boundary state.

13. The apparatus of claim 6, wherein, with the container holding a working amount of the selected photocurable mixture and with the curing light source operated so as to selectively transmit the curing light,
the rotation means is fixed at a point of rotation such that the measurement laser illuminates the interface surface at a selected curing incidence angle during the curing cycle, and
the computer is adapted to determine the intensity of the internally reflected beam of the working amount of the selected mixture at a selected point in the cure cycle, and
the computer is further adapted to determine the refractive index of the working amount of the selected mixture at the selected point in the cure cycle by comparing of the intensity of the internally reflected beam the working amount of the selected mixture at the selected point in the cure cycle with the effective refractive index curve of the mixture in a selected boundary state and then extrapolating the change in refractive index of the mixture at the selected point in the cure cycle.

14. The apparatus of claim 13, wherein, the selected photocurable mixture comprises a photocurable polymeric mixture.

15. The apparatus of claim 14, wherein, the selected photocurable polymeric mixture comprises a photocurable resin or adhesive.

16. The apparatus of claim 13, wherein, the boundary state comprises an uncured state.

17. The apparatus of claim 13, wherein the boundary state comprises an cured state.

18. The apparatus of claim 13, wherein, the selected curing incidence angle comprises the critical incidence angle of the photocurable mixture in a selected boundary state, and
wherein, the boundary state is selected from the group of states including an uncured state and a cured state.

19. The apparatus of claim 2, the photonic curing means comprising:
a source of photonic radiation adapted to emit the curing light beam; and
a light conduit adapted to receive the curing light beam and to emit the curing light beam into a face of the prism.

20. The apparatus of claim 19, wherein the source of photonic radiation comprises a UV lamp adapted to emit a UV light, and
wherein, the light conduit comprises a fiber optic means and a collimator.

21. A method of determining the refractive index of a photocurable polymeric mixture at a selected point during the curing cycle, the method comprising the steps:

(a) providing:
a container adapted to hold a selected photocurable polymeric mixture, the mixture disposed adjacent an interface surface of a prism optically coupled to the container;
a measurement light beam illuminating the interface surface at selectable incidence angles so as to reflect a portion of the measurement light beam as an internally reflected light beam;
a light detection means disposed so as to receive the internally reflected light beam and adapted to measure the intensity of the internally reflected light beam;
a photonic curing means operable to selectively transmit a curing light beam and disposed so as to irradiate the photocurable polymeric mixture through the interface surface with the curing light beam; and
a rotation means adapted to adapted to rotate the container, the prism, and the light detection means relative to the measurement light beam;
(b) selecting a photocurable polymeric mixture;
(c) providing a working amount of the selected mixture disposed within the container;
(d) fixing the rotation means at a point of rotation such that the measurement light beam illuminates the interface surface at a selected curing incidence angle during the curing cycle;
(e) selectively operating the curing light source for a curing cycle so as to selectively transmit the curing light so as to irradiate the photocurable polymeric mixture;
(f) measuring the intensity of the internally reflected beam at a selected point in the cure cycle of the working amount of the selected mixture, and
(g) determining the refractive index of the selected photocurable polymeric mixture at the selected point in the cure cycle by comparing of the intensity of the internally reflected beam the working amount of the selected mixture at the selected point in the cure cycle with the effective refractive index curve of the mixture in a selected boundary state and then extrapolating the change in the refractive index of the mixture at the selected point in the cure cycle.

22. The method of claim 21, the method including the steps of:
providing a test amount of the selected mixture in a boundary state and disposed within the container;
operating the rotation means so as to illuminate the interface surface at each of a plurality of selected incidence angles;
determining the intensity of the internally reflected light beam of the selected mixture in the selected boundary state at each incidence angle selected;
determining, for each selected incidence angle, the effective refractive index and correlating, for each selected incidence angle, the effective refractive index and the intensity of the internally reflected light beam of the mixture in the selected boundary state; and
determining the refractive index of the selected mixture in the selected boundary state.

23. The method of claim 22, wherein, the boundary state comprises an uncured state.

24. The method of claim 22, wherein the boundary state comprises an cured state.

25. The method of claim 22, the method further including the steps:
determining the amount of curing corresponding to the refractive index of the selected photocurable polymeric mixture at the selected point in the cure cycle adjusting a selected processing parameter at the selected point in the cure cycle.

26. The method of claim 25, wherein the adjusted processing parameter is selected from the group of processing parameters including duration of curing light irradiation, intensity of curing light irradiation, operating frequency of curing light, and period of curing light irradiation.

27. A refractometer comprising:
a prism optically coupled via an optical window to a spectroscopic cell adapted to hold a selected photocurable mixture forming an interface with the prism, the prism and cell mounted on a rotation means;
a computer adapted to control the rotation of the rotation means relative to a measurement light source which illuminates the interface at selected incidence angles so as to generate an internally reflected light beam;
a curing light source adapted to transmit a curing light through the prism and into the photocurable mixture and operable to selectively transmit the curing light during a curing cycle;
a light detector mounted on the rotation means and adapted to generate a signal to the computer proportional to the intensity of the internally reflected light beam,
wherein, when a test amount of the selected photocurable mixture in an uncured state is disposed in the cell,
the computer is adapted to rotate the rotation means and to determine the intensity of the internally reflected beam at selected incidence angles, and
the computer is further adapted to determine the refractive index of the uncured photocurable mixture;
wherein, when a working amount of the selected photocurable mixture is disposed in the cell and when the curing light source is operated so as to selectively transmit the curing light,
the computer is adapted to control the rotation means at a fixed point of rotation during the curing cycle corresponding to a selected and fixed incidence angle,
the computer is further adapted to determine the intensity of the internally reflected beam at a selected point in the cure cycle, and
the computer is yet further adapted to determine the refractive index of the polymeric mixture at the selected point in the cure cycle by means of comparison of the intensity of the internally reflected beam of the selected photocurable mixture at a selected point in the cure cycle with previously determined intensities of the internally reflected beam of the selected photocurable mixture in an uncured state at the selected incidence angles and extrapolation of the change in refractive index of the polymeric mixture at the selected point in the cure cycle.

28. The apparatus of claim 27, wherein, when a test amount of the selected photocurable mixture in a cured state is disposed in the cell,
the computer is adapted to rotate the plate and to determine the intensity of the internally reflected beam at selected incidence angles, and
the computer is further adapted to determine the refractive index of the cured photocurable mixture.

29. The apparatus of claim 27, wherein the rotation means comprises a rotating plate,
wherein, the measurement light source comprises a laser adapted to emit a laser light beam,
wherein, curing light source comprises a UV lamp adapted to transmit a UV light via a fiber optic means and a collimator through the prism and into the photocurable mixture, and
wherein, the light detector comprises a photodetector.

30. A refractometer comprising:
a prism having an interface surface optically coupled to spectroscopic cell adapted to hold a photocurable polymeric mixture;
a measurement light source adapted to illuminate the interface surface so as to cause an internally reflected light beam; and
a curing light source adapted to emit a curing light beam
wherein, the prism is disposed so as to receive the curing light beam and to emit the curing light beam from the interface surface so as to irradiate the photocurable mixture with the curing light beam.

31. The apparatus of claim 30, the apparatus further comprising
a light detector disposed so as to receive the internally reflected light beam and adapted to generate a signal to the computer proportional to the intensity of the internally reflected light beam.

* * * * *